United States Patent [19]

Bergomi et al.

[11] Patent Number: 4,663,455
[45] Date of Patent: May 5, 1987

[54] PROCESS FOR THE PREPARATION OF N,N'-TETRATHIODIMORPHOLINE

[75] Inventors: Angelo Bergomi, Akron; Joseph A. Kuczkowski, Munroe Falls, both of Ohio

[73] Assignee: The Goodyear Tire & Rubber Company, Akron, Ohio

[21] Appl. No.: 903,522

[22] Filed: Sep. 4, 1986

[51] Int. Cl.$^4$ .......................................... C07D 295/22
[52] U.S. Cl. ...................................... 544/85; 544/110
[58] Field of Search .......................................... 544/85

[56] References Cited

U.S. PATENT DOCUMENTS 2,351,657  6/1944  Bayes .................................... 544/85
2,911,405  11/1959  Gregg, Jr. ............................ 544/85

Primary Examiner—Robert W. Ramsuer
Attorney, Agent, or Firm—D. O. Nickey

[57] ABSTRACT

There is disclosed a process for the preparation of N,N'-tetrathiodimorpholine wherein an admixture of morpholine and elemental sulfur is oxidized with air or oxygen in the presence of iron salts or iron complexes in combination with zinc compounds such as $ZnCl_2$ and ZnO to yield N,N'-tetrathiodimorpholine.

15 Claims, No Drawings

PROCESS FOR THE PREPARATION OF N,N'-TETRATHIODIMORPHOLINE

TECHNICAL FIELD

The invention relates to a new process for the preparation of N,N'-tetrathiodimorpholine. The invention provides an efficient (improved yields and reduced reaction times) method of preparing N,N'-tetrathiodimorpholine that avoids costly and corrosive chemicals and yields a stable crystalline product with good shelf life. This invention is an improvement to a process described and claimed in U.S. patent application Ser. No. 786,391 filed 10/10/85 by J. J. Tazuma now U.S. Pat. No. 4,621,139.

BACKGROUND OF THE INVENTION

N,N'-tetrathiodimorpholines have found utility in the rubber industry as sulfur donors and vulcanization accelerators. Previous methods to prepare N,N'-tetrathiodimorpholine have included adding sulfur to a solution of morpholine disulfide. The problem with this preparation is that the preparation of morpholine disulfide is expensive and cumbersome. Morpholine disulfide is prepared by the reaction of morpholine and sulfur monochloride in the presence of alkali in an organic solvent. M. C. Throdahl and M. W. Harman, Ind. Eng. Chem., 43, 421 (1951).

Another prior art methodology for the preparation of N,N'-tetrathiodimorpholines involves the use of halopolysulfides and morpholine. This procedure uses the highly toxic and corrosive halopolysulfides, for example, sulfur dichloride and dichloropolysulfides.

U.S. Pat. No. 2,911,405 discloses a process for the preparation of N,N'-tetrathiodimorpholines via insertion of sulfur into N,N'-dithiodimorpholine and Chemical Abstracts 40, 732-9 describes a process wherein morpholine and sulfur are reacted in the presence of lead oxide. None of the prior art discloses or suggests a process for the preparation of N,N'-tetrathiodimorpholine based on the oxidation of a morpholine/sulfur mixture in the presence of iron compounds in combination with zinc compounds such as $ZnCl_2$ and ZnO.

There is a need in the rubber chemical industry for a new proces that efficiently and economically produces N,N'tetrathiodimorpholines which does not require the use of expensive or dangerous starting materials.

DISCLOSURE OF THE INVENTION

There is disclosed a process for the preparation of N,N'-tetrathiodimorpholine which comprises contacting a mixture of morpholine and sulfur at a mole ratio of morpholine to sulfur of from 0.5:1.0 to 5:1 with air or oxygen at atmospheric or superatmospheric pressure at a temperature of from 0° C. to 80° C. in the presence of iron salts or complexes and zinc compounds.

There is further disclosed a process for the preparation of N,N'-tetrathiodimorpholine, the improvement comprising the oxidation of a morpholine sulfur mixture with air or oxygen in the presence of ferric chloride and zinc oxide or zinc chloride.

There is also disclosed a process for the preparation of N,N'-tetrathiodimorpholine which comprises the steps of:

(a) admixing morpholine and sulfur to a mole ratio of morpholine to sulfur of from 0.5:1.0 to 5:1;
(b) contacting the admixture with air or oxygen at atmospheric or elevated pressure and at a temperature from 20° C. to 60° C. in the presence of iron salts or iron complexes and zinc compounds;
(c) isolating N,N'-tetrathiodimorpholine.

Through the process of the instant invention, N,N'-tetrathiodimorpholine is obtained by the reaction of morpholine with sulfur in the presence of air or oxygen. A by-product, morpholinium thiosulfate, is also formed. Morpholinium thiosulfate is the major product when the oxidation is conducted without the addition of iron compounds or zinc compounds. E. M. Peters and W. T. Smith, Jr., Proc. Iowa Acad. Sci. 57, 211 (1950).

An advantage of the instant invention is the use of air or oxygen as the oxidizing agent, thus avoiding costly, corrosive, or toxic chemicals. Through the instant process N,N'-tetrathiodimorpholine can be obtained in greater than 90% selectivity based on reacted morpholine.

Morpholine, the starting material for the instant invention, has the empirical formula $C_4H_9NO$. It has been determined that morpholine from different sources may contain various levels of metal contaminants. The sulfur used in the instant process is conventional rombic sulfur that is in the form of a fine powder. Sulfur normally exists in the $S_8$ rombic form, and then used herein, the term "moles of sulfur" actually refers to gram atoms of sulfur. The mole ratio of morpholine to sulfur can range from 0.5:1.0 to 5.0:1.0. More preferred is the range of 3.0:1.0 to 1.0:1.0.

Representative of the iron salts and iron complexes that are useful in this invention are ferric chloride, ferrous chloride, ferric acetate, ferrous acetate, ferrous ammonium sulfate, ferric bromide, ferrous bromide, ferrous carbonate, ferrocyanides, ferricyanides, ferric fluoride, ferrous flouride, ferric hydroxides, ferrous ferric hydroxide, ferrous hydroxide, ferrous iodide, ferric nitrate, ferrous nitrate, ferric oxalate, ferrous oxalate, ferric oxide, ferrous oxide, ferric sulfate, ferrous sulfate, ferric sulfide, ferrous sulfide, EDTA iron complexes, and others that are apparent to those skilled in the chemistry. The quantity of iron per kilogram of morpholine can range between 0.1 mg and 30 mg. The preferred range is 5 mg to 20 mg.

Representative of the zinc compounds that are useful in this invention are zinc oxide, zince chloride, zinc sulfide, zinc carbonate, zinc fluoride, zinc hydroxide, zinc sulphate and others that are apparent to those skilled in chemistry. The quantity of zinc per kilogram of morpholine can range between 0.1 g and 30 g.

Generally, an admixture of morpholine and sulfur at 20° C. to 60° C. is contacted with oxygen or air at atmospheric or superatmospheric pressure such as ten atmospheres. It should be appreciated that air or air enriched with oxygen at atmospheric or superatmospheric pressure can be employed. Conventional stainless stirred reactors can be used and the reaction is terminated upon the disappearance of sulfur.

After the reaction, the slurry is mixed with a water soluble alcohol, such as methyl, ethyl, propyl or isopropyl. Additionally, this step may be aided by cooling the mixture below room temperature and/or seeding the mixture with N,N'-tetrathiodimorpholine. After a crystallization period, the mixture is treated with water or a dilute caustic solution which dissolves the salts leaving a crystalline product. This product consists mainly of morpholine tetrasulfide with minor amounts of other polysulfides and variable amounts of sulfur related to the morpholine/sulfur ratio in the initial charge. The quantity of sulfur in the final product ranges from 20% for the experiments with a morpholine/sulfur mole ratio of 0.5/1.0 to 5% or less for the experiments with a 2.0/1.0 morpholine/sulfur mole ratio. The residual morpholine present in the filtrate effluent can be recovered by conventional means, such as fractional distillation or solvent extraction and recycled.

BEST MODE FOR CARRYING OUT THE INVENTION

The following examples are offered to further illustrate the novelty and utility of the present invention, but not with the invention of unduly limiting the same.

EXAMPLE 1-4
& Controls 1-5

To a 500 ml, three-necked flask fitted with a high speed stirrer, gas inlet, thermometer and water bath was charged 87 grams (1.0M) of morpholine (supplied by Texaco) 32 g (1.0M) of sulfur and the desired amounts of Fe (as a $FeCl_3$ solution) and ZnO. The resultant mixture was stirred rapidly and oxygen was introduced to the flask. A water bath was used to hold the reaction mixture at about 40° C. The course of the reaction was monitored by following the oxygen absorption rate and by visual inspection of the flask contents. After about one hour most of the sulfur was reacted and the mixture took on a light orange color. After the oxidation the mixture was diluted with 75 ml of methanol with vigorous stirring and cooled to 15° C. and crystallization was allowed to proceed over a 30 minute stirring period. The product was recovered by diluting the crystallized mixture with 150 ml of 3% sodium hydroxide solution, stirring for another 30 minutes at 10°-15° C., and filtered. The product was further washed with water and dried. Different amounts of the zinc salt were used and 5 controls were performed to demonstrate the benefits of this invention. The results from the experimentals and controls are set out in Table I.

EXAMPLES 5-9

Different Morpholine to Sulfur Ratios

To a 500 ml flask equipped with stirrer, thermometer, gas inlet tube, and reflux condenser, were charged 87.1 g (1.0 m) of morpholine, 16.0 g (0.5 m), 48 g (1.5 m) or 32 g (1.0 m) of sulfur, 0.1 g of ZnO and 1 mg of Fe (as a $FeCl_3$ solution). Air was passed through the flask at 40° C. while the mixture was vigorously stirred. Over a period of several hours the sulfur disappeared while the mixture turned dark red. After the disappearance of the sulfur, the reaction was continued until the mixture turned light orange.

After the reaction was complete, an alcohol was added with stirring at room temperature. The product first separated as an oil, which eventually crystallized. The stirring was continued for 30 minutes after the crystallization and water was added. The precipitated N,N'-tetrathiodimorpholine was filtered and washed carefully to remove the morpholine and the other impurities and dried at 40° C. in air. The results from Examples 5-9 are set out in table II.

In Examples 5-9 the morpholine/sulfur molar ratio between 0.5 and 2.0 was investigated. At every ratio the major reaction product was morpholine tetrasulfide, with minor amounts of the tri- and pentasulfide. Occasionally, trace amounts of higher polysulfides were also present. At a 1/1 molar ratio or lower, the product yield was 80% or slightly higher. The purity ranged from 95% for the product obtained at a 2/1 ratio to 80% when the ratio was lowered to 0.5/1. Unreacted sulfur was also present in the final product, its amount ranging from 5% for the experiments run with a 2/1 ratio to 20% at the 0.5/1 ratio. In conclusion, the reaction product consisted mainly of morpholine tetrasulfide with minor amounts of other polysulfides and variable amounts of sulfur related to the initial morpholine/sulfur ratio.

Discussion of Results

The morpholine used in the Controls and the Examples of Table I was of a very high purity and was obtained from the Texaco Chemical Company. In an uncatalyzed experiment, the product was obtained in low yield (54%), Control 1. A long reaction time in excess of three hours was required and the reaction died out before all of the sulfur had reacted.

The addition of iron had a beneficial effect on the reaction from the point of view of the N,N'-tetrathiodimorpholine yield and of the time required. However, a comparison of the data obtained from Texaco morpholine and an identical experiment ran with commercial morpholine from another source showed that the Texaco material had a lower reactivity. This varying behavior is characteristic of morpholine obtained from different sources.

A marked improvement in the yield of N,N'-tetrathiodimorpholine and a reduction in the time required for the reaction was realized when ZnO was used in combination with an iron salt. The tetrasulfide yield increased from about 65% to more than 75% and the reaction time was cut in half, from 2 to 1 hour. A control experiment ran in the presence of ZnO alone gave results identical to those obtained without iron, thus indicating that ZnO by itself is not an effective catalyst of the autoxidation reaction. Besides ZnO, zinc chloride ($ZnCl_2$) was found to have a beneficial effect when used in conjunction with iron. The use of ZnO is, however, preferred since it is a common ingredient of vulcanization recipes.

Compounding Study

A compounding study was conducted to compare the product of the instant invention to known sulfur donor accelerators. It was found to be a good replacement for conventional sulfur donor accelerators in various rubber stocks. The physical properties and state of cure in most instances were nearly identical to those of the commercially available control. Overall, the N,N'-tetrathiodimorpholine prepared according to the instant invention can be considered competitive with other accelerator materials presently used in industry.

Industrial Applicability

The process of the instant invention fulfills a long-felt need in the rubber chemical industry. The importance of amine sulfides as vulcanization accelerators is well established. See M. C. Throdahl and M. W. Harman. Ind. Eng. Chem. 43, 431 (1951). Through the instant process, N,N'-tetrathiodimorpholines can be produced efficiently and economically without the use of corrosive or toxic chemicals.

While certain representative embodiments and details have been shown for the purpose of illustrating the invention, it will be apparent to those skilled in this art that various change and modifications may be made therein.

Having described the invention in such detail so as to allow one skilled in the art to duplicate the same, the inventors herein claim their invention as follows.

TABLE I

| Experimental | Morpholine gms. | Sulfur gms. | Fe, mg | ZnO g | Temp °C. | Reaction Time, hrs | MTS g[a] | Yield %[c] |
|---|---|---|---|---|---|---|---|---|
| Control | | | | | | | | |
| 1 | 87 | 32 | — | — | 41 | 3 | 40.5 | 54.0 |
| 2 | 87 | 32 | — | 0.15 | 41 | 4 | 40.1 | 53.5 |
| 3 | 87 | 32 | 1 | — | 40 | 2 | 48.1 | 64.1 |
| 4 | 87 | 32 | 2 | — | 40 | 2 | 48.6 | 64.8 |
| 5 | 87 | 32 | 3 | — | 40 | 2 | 48.7 | 64.9 |
| Example | | | | | | | | |
| 1 | 87 | 32 | 3 | 2.0 | 40 | 1 | 60.9 | 81.2 |
| 2 | 87 | 32 | 3 | 1.0 | 40 | 1 | 57.5 | 76.7 |
| 3 | 87 | 32 | 3 | 0.15 | 40 | 1 | 56.7 | 75.6 |
| 4 | 87 | 32 | 3 | 2.0[b] | 40 | 1 | 57.5 | 76.7 |

[a] N,N'—tetrathiodimorpholine.
[b] 2.0 g of ZnCl$_2$ was used.
[c] Yield based on sulfur.

TABLE II

| | Preparation of MTS Using Different Molar Ratios of Morpholine to Sulfur | | | | | | | |
|---|---|---|---|---|---|---|---|---|
| Example # | Morpholine gms. | Sulfur gms. | ZnO g | Fe mg | MH/S* mols | MTS** g | MTS Yield | MTS Purity |
| 5 | 87.1 | 16.0 | 0.5 | 1 | 2.0 | 32.0 | 85.3 | 96.3 |
| 6 | 87.1 | 48.0 | 0.5 | 1 | 0.5 | 79.2 | 70.4 | 79.7 |
| 7*** | 87.1 | 32.0 | 0.3 | 1 | 1.0 | 60.3 | 80.4 | 91.8 |
| 8 | 87.1 | 16.0 | 0.1 | 1 | 2.0 | 31.8 | 84.8 | 96.6 |
| 9 | 87.1 | 48.0 | 0.1 | 1 | 0.5 | 72.4 | 64.4 | 83.0 |

*Morpholine/Sulfur Ratio
**Morpholine Tetrasulfide or N,N'—tetrathiodimorpholine
***Average of two experiments

We claim:

1. A process for the preparation of N,N'-tetrathiodimorpholine which comprises contacting a mixture of morpholine and sulfur at a mole ratio of morpholine to sulfur of from 0.5:1.0 to 5:1 with air or oxygen or air enriched with oxygen at atmospheric or superatmosphere pressure at a temperature of from 0° C. to 80° C. in the presence of iron salts or complexes and zinc compounds.

2. The process of claim 1 wherein the iron salt is ferric chloride and the zinc compound is ZnO.

3. The process of claim 1 wherein the iron salt is ferrous chloride and the zinc compound is ZnCl$_2$.

4. The process of claim 6 wherein the reaction is carried out at 20° C. to 60° C.

5. The process of claim 1 wherein oxygen is used at atmospheric or superatmospheric pressure.

6. The process of claim 1 wherein air is used at superatmospheric pressure; the iron salt is ferric chloride and the zinc salt is ZnCl$_2$.

7. The process of claim 1 wherein air enriched with oxygen is used at atmospheric or superatmospheric pressure; the iron salt is ferrous chloride and the zinc compound is ZnO.

8. The process of claim 1 wherein the iron complex is an EDTA complex of an iron salt and the zinc compound is ZnO.

9. The process of claim 1 wherein the mole ratio of morpholine to sulfur can range from 3.0:1.0 to 1.0:1.0.

10. The process of claim 1 wherein 0.1 to 30 mg of the iron salt and 0.3 to 30 g of the zinc compound per kg of morpholine is used.

11. The process of claim 1 wherein the amount of iron is from 5 to 20 mg per kg of morpholine and the amount of zinc is from 5 to 20 g per kg of morpholine.

12. There is also disclosed a process for the preparation of N,N'-tetrathiodimorpholine which comprises the steps of:
    (a) admixing morpholine and sulfur to a mole ratio of morpholine to sulfur of from 0.5:1.0 to 5:1;
    (b) contacting the admixture with air or oxygen at atmospheric or elevated pressure and at a temperature from 20° C. to 60° C. in the presence of iron salts or complexes and zinc compounds;
    (c) isolating N,N'-tetrathiodimorpholine.

13. The process of claim 12 wherein the mole ratio of morpholine to sulfur can range from 3.0:1.0 to 1.0:1.0.

14. The process of claim 12 wherein 0.1 to 30 mg of the iron salt and 0.3 to 30 g of the zinc compound per kg of morpholine is used.

15. The process of claim 12 wherein the amount of iron is from 5 to 20 mg per kg of morpholine and the amount of zinc is from 5 to 20 g per kg of morpholine.

* * * * *

UNITED STATES PATENT AND TRADEMARK OFFICE
CERTIFICATE OF CORRECTION

PATENT NO. : 4,663,455

DATED : May 5, 1987

INVENTOR(S) : Bergomi et al

It is certified that error appears in the above-identified patent and that said Letters Patent is hereby corrected as shown below:

In Column 1 at line 46 kindly delete the word, "N,N'tetrathiodimorpholines" and insert therefor --N,N'-tetrathiodimorpholines"--.

In Column 4 at line 61, kindly delete the "." and insert therefor --,--.

In Column 6 at line 43, kindly delete the phrase, "There is also disclosed a" and insert therefor --A--.

Signed and Sealed this

Twenty-fourth Day of November, 1987

*Attest:*

DONALD J. QUIGG

*Attesting Officer*  *Commissioner of Patents and Trademarks*